United States Patent [19]

Bänziger et al.

[11] Patent Number: 5,352,801
[45] Date of Patent: Oct. 4, 1994

[54] PROCESS FOR THE PRODUCTION OF OPTICALLY-ACTIVE 4-AMINO-3-HYDROXYCARBOXYLIC ACIDS

[75] Inventors: Markus Bänziger, Brig-Glis; John McGarrity; Thomas Meul, both of Visp, all of Switzerland

[73] Assignee: Lonza Ltd., Gampel/Valais, Switzerland

[21] Appl. No.: 120,793

[22] Filed: Sep. 15, 1993

Related U.S. Application Data

[62] Division of Ser. No. 932,587, Aug. 20, 1992, Pat. No. 5,286,650.

[30] Foreign Application Priority Data

Aug. 22, 1991 [CH] Switzerland .................. 2471/91

[51] Int. Cl.$^5$ ........................................ C07D 207/273
[52] U.S. Cl. .................................................. 548/544
[58] Field of Search ....................................... 548/544

[56] References Cited

U.S. PATENT DOCUMENTS

4,876,343 10/1989 Hodges et al. .................... 544/168

FOREIGN PATENT DOCUMENTS

| 0195717 | 3/1986 | European Pat. Off. . |
| 0216324 | 9/1986 | European Pat. Off. . |
| 0210896 | 2/1987 | European Pat. Off. . |
| 0358128 | 1/1989 | European Pat. Off. . |
| 0346852 | 6/1989 | European Pat. Off. . |

OTHER PUBLICATIONS

Katsuki et al., Bul. Chem. Soc. Japan, vol. 94, No. 11, (1976), pp. 3287 to 3290.

Altenbach, Nach. Aus Che., Tech. und Lab., vol. 36, No. 7, (1988), pp. 756 to 758.

H. Pielatzik et al., "Methoden Der Organischen Chemie", Houben-Weyl, 4th Ed., vol. E5, (1985), pp. 633 to 656.

G. Hesse, "Methoden Der Organischen Chemie", Houben-Weyl, 4th Ed., vol. VI/1d, (1978), pp. 108 to 115.

*Primary Examiner*—David B. Springer
*Attorney, Agent, or Firm*—Fisher, Christen & Sabol

[57] ABSTRACT

Starting from 5-alkylidene or 5-benzylidenetetramic acid optically-active 4-amino-3-hydroxy-carboxylic acids are produced in the (rel-3R,4R) configuration, especially statine. The synthesis process includes the O-acylation of the tetramic acid to the corresponding 4-acyloxy-3-pyrrolin-2-one, a stereoselective hydrogenation to (rel-4R,5R)-4-acyloxy-5-alkyl or 5-benzylpyrrolidin-2-one and an enantioselective enzymatic hydrolysis of the (4R,5R)-enantiomer to the corresponding 4-hydroxypyrrolidin-2-one. The nonhydrolyzed enantiomer is separated and converted into the target compound with (3S,4S) configuration by hydrolytic cleavage of the lactam ring and the ester function and optionally introduction of an amino protective group. Analogously the (3R,4R)-enantiomer can be obtained from the 4-hydroxypyrrolidin-2-one from the enzymatic hydrolysis. The 4-amino-3-hydroxycarboxylic acids producible according to the invention are the structural elements of enzyme inhibitors.

4 Claims, No Drawings

PROCESS FOR THE PRODUCTION OF OPTICALLY-ACTIVE 4-AMINO-3-HYDROXYCARBOXYLIC ACIDS

This application is a divisional of Ser. No. 07/932,587, filed Aug. 20, 1992, now U.S. Pat. No. 5,286,650.

BACKGROUND OF THE INVENTION

The invention relates to a process for the production of optically-active 4-amino-3-hydroxycarboxylic acids and their N-protected derivatives.

The products of the process according to the invention have the general formula:

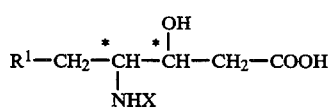

wherein $R^1$ is an optionally branched and/or substituted alkyl group with 1 to 10 C atoms or an optionally substituted aryl, arylalkyl or cycloalkyl group and X is a hydrogen or an amino protective group. These compounds have two chiral centers and, therefore, can occur in 4 stereoisomeric forms each.

The process according to the invention allows production alternatively of the (3R,4R) or (3S,4S) enantiomer. These two enantiomers are comprised by the stereochemical designations (rel-3R,4R) or (3R*,4R*). The first of the two designations is used below.

Some of these compounds, especially those with $R^1$=isopropyl or cyclohexyl, are of interest as the structural element of peptides, which have enzyme inhibiting effects. But only the (3S,4S)-stereoisomer is effective in this connection. Especially (3S,4S)-4-amino-3-hydroxy-6-methylheptanoic acid, known by the trivial name statine, which is contained in the renin inhibitor pepstatine, already was the aim of numerous different synthesis processes [see, for example, European Patent No. 0210896; H. J. Altenbach, Nachr. Chem. Tech. Lab., 36, (1988), pages 756 to 758; M. Saiah et al., Tetrahedron Asymmetry, 2, (1991), pages 111 and 112, as well as literature cited there]. However, these syntheses are only poorly suitable or unsuitable for the economical production of large amounts of different substituted 4-amino-3-hydroxycarboxylic acids, because they require partly expensive starting materials, partly are suitable only on a laboratory scale and partly the necessary starting materials are available at all only for specific radicals $R^1$ of general formula I.

BROAD DESCRIPTION OF THE INVENTION

The main object of the invention, therefore, is to provide a process for the production of optically-active (rel-3R,4R)-4-amino-3-hydroxycarboxylic acids, that requires only reasonably priced starting materials and that can be performed on a large scale. Other objects and advantages of the process and compounds of the invention are set out herein or are obvious herefrom to one skilled in the art.

The objects and advantages of the invention are achieved by the process and compounds of the invention.

The invention involves a process for the production of optically-active (rel-3R,4R)-4-amino-3-hydroxycarboxylic acids of the general formula:

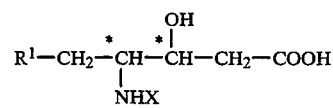

wherein $R^1$ is an optionally branched and/or substituted alkyl group with 1 to 10 C atoms or an optionally substituted aryl, arylalkyl or cycloalkyl group and X is hydrogen or an amino protective group. A substituted tetramic acid of the general formula:

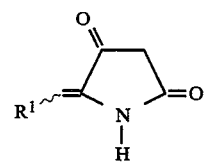

wherein $R^1$ has the above-mentioned meaning, is acylated with a carboxylic acid or a carboxylic acid derivative of the general formula:

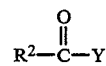

wherein $R^2$ is an optionally branched and/or substituted alkyl group with 1 to 10 C atoms or an aryl group and Y is halogen, OH or OC(=O)$R^2$ to a compound of the general formula:

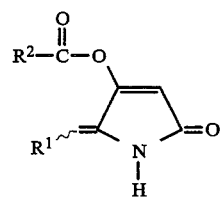

Then the latter is stereoselectively hydrogenated to the corresponding enantiomeric pyrrolidin-2-ones of the general formula:

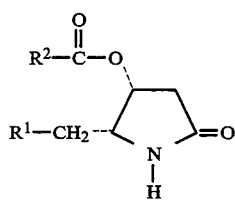

and

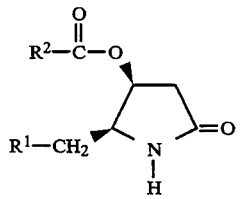

The (4R,5R)-enantiomer (Va) is hydrolyzed enantioselectively. with a lipase to the corresponding (4R,5R)-4-hydroxypyrrolidin-2-one of the general formula:

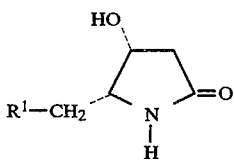
VI and separated from the nonhydrolyzed (4S,5S)-enantiomer (Vb). Then alternatively the acyloxy compound Vb or the hydroxy compound VI is hydrolyzed with cleavage of the lactam ring to the target compound I (X=H) and optionally converted (e.g., according to known processes) into the corresponding N-protected form.

Preferably butyric acid or a derivative of butyric acid is used as the carboxylic acid or carboxylic acid derivative (III), respectively. Preferably butyryl chloride is used as the butyric acid derivative. Preferably the stereoselective hydrogenation is performed with a catalyst of the group of palladium or rhodium catalysts or of palladium/rhodium mixed catalysts. Preferably a supported palladium catalyst is used as catalyst. Preferably a lipase from *Candida cylindracea* is used as the lipase. Preferably, after the enantioselective hydrolysis, the nonhydrolyzed (4S,5S)-enantiomer (Vb) is reacted to the target compound. Preferably after the cleavage of the lactam ring, the tert-butoxycarbonyl group is introduced as the amino protective group X. Preferably a 5-isobutylidene- ($R^1$=isopropyl) or 5-benzylidenetetramic acid-($R^1$=phenyl) is used as the substituted tetramic acid (II).

The invention also includes (4S,5S)-4-acyloxypyrrolidin-2-ones of the general formula:

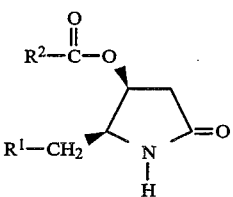
Vb wherein $R^1$ is an optionally branched and/or substituted alkyl group with 1 to 10 C atoms or an optionally substituted aryl, arylalkyl or cycloalkyl group and $R^2$ is an optionally branched and/or substituted alkyl group with 1 to 10 C atoms or an optionally substituted aryl group. Preferably $R^1$ is isopropyl, phenyl or cyclohexyl. Preferably $R^2$ is propyl.

DETAILED DESCRIPTION OF THE INVENTION

It has been found that, obtainable from 5-alkylidene tetramic acids of the general formula:

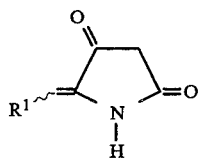
II or the tautomeric form:

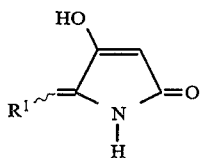
II' in which $R^1$ has the above-mentioned meaning, and carboxylic acids or carboxylic acid derivatives of the general formula:

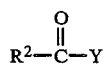
III in which $R^2$ is an optionally branched and/or substituted alkyl group with 1 to 10 C atoms or an aryl group and Y is halogen, OH or OC(=O)$R^2$, 4-O-acyl-5-alkylidenetetramic, acids of the general formula:

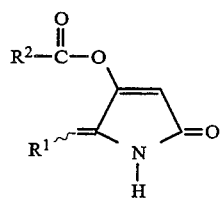
IV wherein $R^1$ and $R^2$ have the above-mentioned meanings, can be hydrogenated with good stereoselectivity to a mixture, which consists basically of the (4RS,5RS)-racemate of the corresponding 4-acyloxy-pyrrolidin-2-ones of the general formulas:

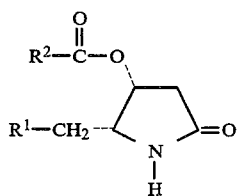
Va and

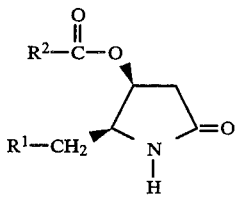
Vb wherein $R^1$ and $R^2$ have the above-mentioned meanings and of small amounts of the corresponding (4RS,5SR)-racemate. The undesirable (4RS,5SR)-racemate can be easily separated.

Further it was found that the enantiomer with the (4R,5R)-configuration (Va) in the presence of lipases can be selectively deacylated. Because of the great difference in the polarity (4R,5R)-4-hydroxypyrrolidin-2-one of the general formula:

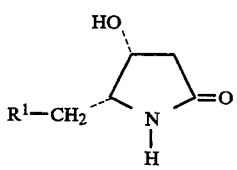

wherein R¹ has the above-mentioned meaning, can be easily separated.

The unreacted (4S,5S)-4-acyloxypyrrolidin-2-one (Vb) can finally be converted, analogously to known processes with cleavage of the acyl group and opening of the lactam ring, to the corresponding (3S,4S)-4-amino-3-hydroxycarboxylic acid (I).

As an alternative to the above the corresponding (3R,4R)-4-amino-3-hydroxycarboxylic acid (I) can be obtained from (4R,5R)-4-hydroxypyrrolidin-2-one (VI), formed in the enzymatic deacylation, after its isolation by hydrolytic opening of the lactam ring.

The 5-alkylidenetetramic acids (II) necessary for the process according to the invention can be produced according to known processes from 4-alkoxy-3-pyrrolin-2-ones and aldehydes (European Published Patent Application No. 0358128).

It was found that their synthesis can be simplified significantly by the production of 4-alkoxy-3-pyrrolin-2-one and the reaction with aldehyde being performed in one pot without isolation of the intermediate products. For this purpose an (E)-3-alkoxy-4-chlorobut-2-enoic acid alkyl ester, which is easily available from 4-chloroacetoacetyl chloride (European Published Patent Application No. 0346852), is cyclized with aqueous ammonia in a way known in the art (European Published Patent Application No. 0216324) to the corresponding 4-alkoxy-3-pyrrolin-2-one and the latter is condensed without isolation in the presence of a strong base with the aldehyde to the corresponding 4-alkoxy-5-alkylidene-3-pyrrolin-2-one. Preferably (E)-4-chloro-3-methoxybut-2-ene methyl ester is used as the initial material and sodium hydroxide as the strong base.

The thus-obtained 4-alkoxy-5-alkylidene-3-pyrrolin-2-one can be converted without isolation in a way known in the art by acid hydrolysis into 5-alkylidenetetramic acid (II).

For acylation of 5-alkylidenetetramic acid (II) to 4-acyloxy compounds (IV), which can be understood to be mixed anhydrides of the corresponding carboxylic acids and tetramic acids or as enolic esters, basically every process for the production of mixed carboxylic acid anhydrides or carboxylic acid-enolic esters from the corresponding carboxylic acids or carboxylic acid derivatives can be used. This includes, for example, the reaction with the carboxylic acids in the presence of carbodiimides or 1-acylimidazoles, the reaction with carboxylic acid anhydrides or with carboxylic acid halides [see, H. Pielatzik et al. in "Methoden der Organischen Chemie" (Methods of Organic Chemistry), (Houben-Weyl), 4th ed., Vol. E5, Stuttgart (1985), pages 633 to 656, and G. Hesse in "Methoden der Organischen Chemie", (Houben-Weyl), 4th ed , Vol. VI/1d, Stuttgart, (1978), pages 108 to 115].

A preferred embodiment uses carboxylic acid halides, especially carboxylic acid chlorides, in the presence of tertiary amines, such as, triethylamine or pyridine. Instead of free tetramic acids (II), their enolates for example the sodium salts can also be used.

As carboxylic acids or carboxylic acid derivatives (III), aliphatic or aromatic carboxylic acids, especially $C_2$–$C_{11}$-alkanoic acids or benzoic acids, or their derivatives, can be used for the acylation, especially preferred is butyric acid or butyryl chloride.

The 4-acyloxy compounds (IV) were hydrogenated according to the invention and two asymmetric centers were formed. The hydrogenation takes place largely stereoselectively so that, aside from a little (4RS,5SR)-diastereomer, mainly the (racemic) (4RS,5RS)-pyrrolidin-2-one (Va/Vb) results.

As the catalyst for the hydrogenation, preferably a supported palladium catalyst is used, for example, 5 percent of palladium on activated carbon. Instead of palladium, rhodium, for example, rhodium on aluminum oxide, or a Pd/Rh-catalyst, can also be used. As the solvent for the hydrogenation, advantageously nonpolar or polar aprotic solvents, for example, toluene, ethyl acetate or tetrahydrofuran, are used. Protic solvents, such as, alcohols, can also be used but such lead to poorer yields. The hydrogenation is preferably performed at about room temperature and under medium pressure of, for example, 2 MPa (20 bar).

(4RS,5SR)-pyrrolidin-2-ones as well as hydrogenolysis products occasionally resulting as by-products in the hydrogenation can easily be separated in the working up, for example, by simple recrystallization in which they remain in the mother liquor.

The racemate from the (4R,5R)- and the (4S,5S)-pyrrolidin-2-one (Va/Vb) is enantioselectively deacylated according to the invention with an esterase. As the esterase a lipase is suitably used, preferably a lipase from Candida cylindracea. This lipase enantioselectively hydrolyzes the (4R,5R)-4-acyloxypyrrolidin-2-one (Va) to the corresponding 4-hydroxy compound. This deacylation is advantageously performed in an aqueous medium at a pH near the neutral point, preferably at pH 6 to 8, to suppress a non-enzymatic deacylation or hydrolysis. The temperature is suitably at 0° to 40° C., preferably at 0° to 25° C. During the reaction the pH is maintained constant preferably by a suitable control unit ("pH-Stat") by adding a strong base. As the strong base preferably sodium hydroxide solution is used. The reaction conversion can be determined by the amount of base added. Suitably the reaction is terminated after a conversion of about 50 percent of the total amount used (Va+Vb). Depending on whether the nonhydrolized or the hydrolized enantiomer is to be processed further, the reaction advantageously is performed up to a conversion of a little more than 50 percent or somewhat less than 50 percent to obtain a product with the highest possible optical purity.

The separation of the hydroxy compound (VI) from the acyloxy compound (Vb) is advantageously performed by extraction with a solvent of little polarity, for example, toluene. The hydroxy compound, in this case remains in the aqueous phase, while the acyloxy compound changes into the organic phase.

The optically active acyloxy compound or hydroxy compound produced according to the invention is finally converted analogously to known processes (European Published Patent Application No. 0210896) by hydrolysis of the lactam ring and optionally of the ester function into the target compound. Preferably an acid is used as the catalyst for the acid hydrolysis, especially preferred is hydrobromic acid.

The unprotected 4-amino-3-hydroxycarboxylic acids tend toward spontaneous lactam formation and therefore advantageously are provided with a protective group on the amino group. Such protective groups and the methods for their introduction and removal are known to one skilled in the art; only the tert-butoxycarbonyl group is to be mentioned here as an example. Instead of the amino group, the carboxyl group can also be protected, for example, by esterification.

The following examples illustrate the process according to the invention.

EXAMPLE 1

(Z)-5-isobutylidene-4-methoxy-3-pyrrolin-2-one 120 g of (E)-2-chloro-3-methoxybut-2-enoic acid methyl ester was instilled in 200 ml of concentrated aqueous ammonia solution at 65° to 70° C. with constant passing through of ammonia gas within 3 hours. The reaction mixture was stirred another 1.5 hours at this temperature and then refluxed another 0.5 hour. After cooling to room temperature, 450 ml of 1M sodium hydroxide solution was added and the pH was brought to greater than 13 by the further addition of 33 percent sodium hydroxide solution. Then 50 g of isobutyraldehyde was added and the reaction mixture was heated to 60° C. with stirring for 6 hours. After cooling to room temperature, the precipitated product was filtered off, washed with cold water and dried in a vacuum drying cabinet. The yield of the title compound was 93.2 g (80 percent of theory). The title compound had a melting point of 140.5° to 141.1° C. (from diethyl ether).

EXAMPLE 2

(Z)-5-Isobutylidenepyrrolidine-2,4-dione (II, $R^1$=isopropyl)

50 g of finely powdered (Z)-5-isobutylidene-4-methoxy-3-pyrroline-2-one was stirred with 500 ml of concentrated hydrochloric acid for 5 hours at room temperature. The mixture was then stirred 5 hours at room temperature and slowly mixed with 1 liter of 14 percent sodium hydroxide solution. The precipitated yellow product was filtered off, washed with cold water and dried in a vacuum drying cabinet. The yield of the title compound was 42.0 g (92 percent of theory). The title compound had a melting point of 134° to 136° C. (THF/hexane).

EXAMPLE 3

(Z)-4-Butyryloxy-5-isobutylidene-3-pyrrolin-2-one (IV, $R^1$=isopropyl, $R^2$=propyl)

31.8 g of (Z) -5-isobutylidenepyrrolidine-2,4-dione was suspended in 318 ml of dichloromethane and cooled to −5° C. Then first 23.22 g of butyryl chloride was added and then 27.32 g of triethylamine was added. After the addition the mixture was stirred another 10 minutes at 0° C., then diluted with 100 ml of dichloromethane, and washed twice with 100 ml of 5 percent $NaHCO_3$ solution each and twice with 100 ml of 0.4M hydrochloric acid each. The aqueous phases were extracted separately with dichloromethane and the combined organic phases were dried on magnesium sulfate. After the distilling off of the solvent, the crude product (46 g) was recrystallized from hexane. The yield of the title compound was 38.8 g (84 percent of theory). The title compound had a melting point of 111° to 112° C. Other data concerning the title compound was:

$^1$H-NMR ($CDCl_3$; 400 MHz): 1.03 (t, J=7.5, 3H), 1.12 (d, J=6.6, 6H), 1.77 (m, 2H), 2.56 (t, J=7.5, 2H), 2.78–2.83 (m, 1H), 5.35 (d, J=10, 1H), 6.15 (br.s, 1H), 9.91 (br.s, 1H).

EXAMPLE 4

(4RS,5RS)-4-Butyryloxy-5-isobutylpyrrolidin-2-one (Va/Vb, $R^1$=isopropyl, $R_2$=propyl)

30.0 g of (Z)-4-butyryloxy-5-isobutylidene-3-pyrrolin-2-one (produced according to Example 3) was dissolved in 300 ml of toluene, mixed with 3.0 g of palladium/activated carbon(5 percent of pf Pd) and hydrogenated for 24 hours in an autoclave at 2 MPa (20 bar). Then the catalyst was filtered off, the filtrate was concentrated by evaporation and the residue was recrystallized from hexane. The yield of the title compound was 23.50 g (77 percent of theory). The title compound had a melting point of 101.5° to 102.7° C. Other data concerning the title compound was:

$^1$H-NMR ($CDCl_3$; 400 MHz): 0.91–0.98 (m, 9H), 1.35–1.71 (m, 5H), 2.29–2.36 (m, 3H), 2.71 (dd, J=6.4, 17.6, 1H), 3.88–3.93 (m, 1H), 5.40–5.43 (m, 1H), 7.49 (br.s, 1H).

EXAMPLE 5

(4S,5S)-4-Butyryloxy-5-isobutylpyrrolidin-2-one (Vb, $R^1$=isopropyl, $R^2$=propyl)

20 g of (4RS,5RS)-4-butyryloxy-5-isobutylpyrrolidin-2-one (produced according to Example 4) and 2 g of *Candida cylindracea* lipase (Biocatalysts) were stirred in 100 ml of water at room temperature. The pH of the suspension was held constant at 7 by the addition of 1M sodium hydroxide solution. After 70 hours and a consumption of 47.36 ml of 1M sodium hydroxide solution (corresponding to 53.8 percent conversion), the reaction was terminated. The reaction mixture was diluted with 200 ml of water and extracted once with 400 ml and another two times with 200 ml of toluene each. The combined toluene phases were concentrated by evaporation in a vacuum and the residue was dried in a high vacuum. The yield of the title compound was 8.55 g (85.5 percent, relative to one enantiomer). The title compound had a melting point of 94.9° to 95.3° C. Other data concerning the title compound was:

$[\alpha]_D^{20}$: −3.9° (c=1.0; $CHCl_3$)

ee-value (GC, Lipodex Ⓡ D-column)>99 percent

EXAMPLE 6

(3S,4S)-4-(tert-Butoxycarbonylamino-3-hydroxy-6-methyl heptanoic acid (boc-Statine) (I, $R^1$=isopropyl, X=tertbutoxy-carbonyl)

3.0 g of (4S,5S)-4-butyryloxy-5-isobutylpyrrolidin-2-one (produced according to Example 5) was stirred for 24 hours in 30 ml of 48 percent aqueous hydrobromic acid at 75° C. After cooling to room temperature, the mixture was diluted with 30 ml of water and was extracted three times with 20 ml of diethyl ether each to remove the butyric acid. The aqueous phase was cooled to −10° C. and adjusted to pH 10 with 33 percent sodium hydroxide solution. Then 20 ml of tetrahydrofuran and 2.9 g of di-tert-butyl dicarbonate were added. The mixture was allowed to react 94 hours at room temperature and the pH was held constant by the addition of 1M NaOH. Then the mixture was acidified to pH 1.4 with 16 percent hydrochloric acid and quickly extracted three times with 100 ml of diethyl ether each. The ether phase was dried on magnesium sulfate and concentrated by evaporation in a vacuum. The residue was purified by column chromatography on silica gel (hexane/ethyl acetate/acetic acid 6:4:0.1). The yield of the title compound was 2.09 g (58 percent of theory). The title compound had a melting point of 120.2° to 120.9° C. (acetone/hexane). Other data concerning the title compound was:

$[\alpha]_D^{20}$: −40.3° (c=1.0; CH$_3$OH)

$^1$H-NMR (d$_6$-DMSO; 400 MHz): 0.83–0.88 (m, 6H), 1.22–1.29 (m, 2H), 1.38 (s, 9H), 1.53–1.57 (m, 1H), 2.12 (dd, J=15.5, 9.1, 1H), 2.34 (dd, J=15.5, 3.8, 1H), 3.49–3.53 (m, 1H), 3.79–3.82 (m, 1H), 6.24 (d, J=9.1, 1H).

EXAMPLE 7

(Z)-5-Benzylidene pyrrolidin-2,4-dione (II, R$^1$=phenyl)

133 g of concentrated aqueous ammonia solution was heated to 65° to 70° C. 75 g of (E)-2-chloro-3-methoxybut-2-enoic acid methyl ester was instilled for 3 hours with constant passing through of ammonia gas. The mixture was stirred another 45 minutes at this temperature, heated 30 minutes to reflux temperature and then cooled to room temperature. After the addition of 300 ml of water and 50 ml of 33 percent sodium hydroxide solution, 46.4 g of benzaldehyde was added. The mixture was heated for 6 hours at 60° C. under stirring and then cooled to room temperature. Then 688 ml of concentrated hydrochloric acid was added and the reaction mixture was stirred for 22 hours at 40° C. After cooling to room temperature, the yellow product was filtered off, washed with cold water and dried in a vacuum drying cabinet. The yield of the title compound was 74.66 g (88 percent of theory). The title compound had a melting point of 186° to 187° C. (THF/hexane).

EXAMPLE 8

(Z)-5-Benzylidene-4-butyryloxy-3-pyrrolin-2-one (IV, R$^1$=phenyl, R$^2$=propyl)

To a suspension of 67.0 g of (Z)-5-benzylidene pyrrolidin-2,4-dione cooled to 0° C. in 670 ml of dichloromethane, 40.0 g of butyryl chloride and then 47.1 g of triethyl amine were added and the mixture was stirred another 5 minutes at 0° C. Then the mixture washed twice with 200 ml of 5 percent NaHCO$_3$ solution each and then twice with 200 ml of 0.5M hydrochloric acid each. The aqueous phases were extracted separately with dichloromethane. The combined organic phases were dried on magnesium sulfate and concentrated by evaporation in a vacuum. The residue was recrystallized from 230 ml of toluene. The yield of the title compound was 67.25 g (73 percent of theory). The title compound had a melting point of 139.8° to 141.5° C. Other data concerning the title compound was:

$^1$H-NMR (CDCl$_3$; 400 MHz): 1.03 (t, J=7.4, 3H), 1.78 (m, 2H), 2.58 (t, J=6.7, 2H), 6.20 (s, 1H), 6.30 (s, 1H), 7.28–7.50 (m, 5H), 9.20 (br.s, 1H).

EXAMPLE 9

(4RS,5RS)-5-Benzyl-4-butyryloxypyrrolidin-2-one (Va/Vb, R$^1$=phenyl, R$^2$=propyl)

46.66 g of (Z)-5-benzylidene-4-butyryloxy-3-pyrrolin-2-one (produced according to Example 8) was suspended in 467 ml of toluene and hydrogenated for 28 hours with 4.67 g of palladium/activated carbon (5 percent of Pd) in an autoclave at room temperature and 2 MPa (20 bar). Then the catalyst was filtered off and the filtrate was concentrated by evaporation in a vacuum. The residue was recrystallized from diisopropyl ether. The yield of the title compound was 32.88 percent (69 percent of theory). The title compound had a melting point of 85.6° to 87° C. Other data concerning the title compound was:

$^1$H-NMR (CDCl$_3$, 400 MHz): 0.98 (t, J=7.3, 3H) 1.69 (sext., J=7.3, 2H), 2.34–2.41 (m, 3H), 2.68–2.77 (m, 2H), 2.92 (dd, J=14.0, 5.1, 1H), 4.07–4.18 (m, 1H), 5.40–5.48 (m, 1H), 6.04 (br.s, 1H), 7.16–7.34 (m, 5H).

EXAMPLE 10

(4S,5S)-5-Benzyl-4-butyryloxypyrrolidin-2-one (Vb, R$^1$=phenyl, R$^2$=propyl)

In a two-phase system of 145 ml of water and 36 ml of toluene, 21.14 g of (4RS,5RS)-5-benzyl-4-butyryloxypyrrolidin-2-one (produced according to Example 9) and 4.22 g of *Candida cylindracea* lipase (Biocatalysts) were reacted analogously to Example 5. After 116 hours and the consumption of 47.01 ml of 1M sodium hydroxide solution (corresponding to 58 percent conversion), the reaction was terminated. The reaction mixture was diluted with 600 ml of toluene and 250 ml of water and stirred vigorously for 30 minutes. The phases were separated and the aqueous phase was extracted with 300 ml of toluene. The combined toluene phases were concentrated by evaporation in a vacuum, the residue was taken up in 170 ml of toluene, washed three times with 40 ml of water each and again concentrated by evaporation in a vacuum. The thus-obtained crude product was recrystallized from diisopropyl ether. The yield of the title compound was 7.80 g (74 percent relative to one enantiomer). The title compound had a melting point of 78.9° to 79.2° C. Other data concerning the title compound was:

$[\alpha]_D^{20}$: −89.0 ° (c=1.0; CHCl$_3$)

EXAMPLE 11

(3S,4S)-4-(tert-Butoxycarbonyamino)-3-hydroxy-5-phenylpentanoic acid (I, R$^1$=phenyl, X=tert-butoxycarbonyl)

1.0 g of (4S,5S)-5-benzyl-4-butyryloxypyrrolidin-2-one (produced according to Example 10) was stirred for 20 hours at 80° C. in 10 ml of 48 percent aqueous hydrobromic acid. The mixture was then cooled to room temperature, diluted with 10 ml of water and extracted three times with 20 ml of diethyl ether each for removal of the butyric acid. The ether phase was discarded. The aqueous phase was cooled to −5° C. and adjusted to pH 10 with 33 percent sodium hydroxide solution. Then 20 ml of tetrahydrofuran and 0.86 g of di-tert-butyl dicarbonate were added and the mixture was brought to reaction for 24 hours at room temperature and a constant pH of 10. Then the mixture was acidified with 1M hydrochloric acid to pH 1 and extracted three times with 50 ml of diethyl ether each. The combined ether phases were dried on magnesium sulfate and concentrated by evaporation in a vacuum. The residue was purified by column chromatography on silica gel (hexane/ethyl acetate/acetic acid 10:10:0.25). The yield of the title compound was 0.64 g (54 percent of theory). The title compound had a melting point of 153.2° to 153.4° C. (CHCl$_3$/hexane). Other data concerning the title compound was:

$[\alpha]_D^{20}$: −37.7° (c=1.1; CH$_3$OH)

$^1$H-NMR (CDCl$_3$, 60° C.; 400 MHz): 1.40 (s, 9H), 2.40–2.66 (m, 2H), 2.86–2.96 (m, 2H), 3.66–3.82 (m, 1H), 3.96–4.07 (m, 1H), 4.82–5.00 (br.s, 1H), 7.12–7.35 (m, 5H).

EXAMPLE 12

(4S,5S)-4-Butyryloxy-5-(cyclohexylmethyl)pyrrolidin-2-one (Vb, $R^1$=cyclohexyl, $R^2$=propyl 1.0 g of (4S,5S)-5-benzyl-4-butyryloxypyrrolidin-2-one (produced according to Example 10) was dissolved in 10 ml of ethyl acetate, mixed with 100 mg of rhodium/activated carbon (5 percent of Rh, Johnson Matthey Type 20A) and hydrogenated for 20 hours in an autoclave at room temperature at 2 MPa (20 bar). Then the catalyst was filtered off and the filtrate was concentrated by evaporation in a vacuum. The yield of the title compound was 1.0 g of viscous oil (about 98 percent). Other data concerning the title compound was:

$^1$H-NMR (CDCl$_3$, 300 MHz): 0.8–1.35 (m, 9H), 1.45 (t, 2H), 1.58–1.80 (m, 7H), 2.22–2.40 (m, 3H), 2.70 (dd, 1H), 3.85–3.98 (m, 1H), 5.35–5.45 (m, 1H), 6.35 (br.s, 1H).

What is claimed is:

1. (4S, 5S)-4-Acyloxypyrrolidin-2-one of formula:

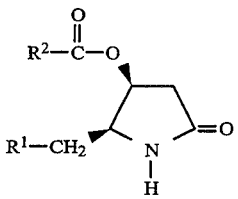

Vb wherein $R^1$ is a branched or a straight chain alkyl group with 1 to 10 C atoms or an aryl, an arylalkyl or a cycloalkyl group and $R^2$ is a branched or a straight chain alkyl group with 1 to 10 C atoms or an aryl group.

2. The compound according to claim 1 wherein $R^1$ is isopropyl, phenyl or cyclohexyl.

3. The compound according to claim 2 wherein $R^2$ is propyl.

4. The compound according to claim 1 wherein $R^2$ is propyl.

* * * * *